United States Patent [19]

Tsuchiya et al.

[11] Patent Number: 5,962,068

[45] Date of Patent: Oct. 5, 1999

[54] WATER-ABSORPTIVE COMPOSITE AND PROCESS FOR PRODUCING THE SAME

[75] Inventors: Hiroyoshi Tsuchiya; Masayuki Yamashita; Kiichi Itoh, all of Yokkaichi, Japan

[73] Assignee: Mitsubishi Chemical Corporation, Tokyo-To, Japan

[21] Appl. No.: 09/129,874

[22] Filed: Aug. 6, 1998

Related U.S. Application Data

[62] Division of application No. 08/665,416, Jun. 18, 1996, abandoned.

[30] Foreign Application Priority Data

Jun. 19, 1995 [JP] Japan ................................ 7-151509
May 30, 1996 [JP] Japan ................................ 8-136386

[51] Int. Cl.$^6$ ................................................ B05D 1/12
[52] U.S. Cl. .................... 427/180; 427/288; 427/389.9; 442/118; 442/417
[58] Field of Search .................... 427/180, 288, 427/389.9; 442/118, 417

[56] References Cited

U.S. PATENT DOCUMENTS

| | | | |
|---|---|---|---|
| 4,605,401 | 8/1986 | Chmelir et al. | 604/368 |
| 4,738,867 | 4/1988 | Itoh et al. | 427/44 |
| 5,230,959 | 7/1993 | Young, Sr. et al. | 428/372 |

*Primary Examiner*—Christopher Raimund
*Attorney, Agent, or Firm*—Oblon, Spivak, McClelland, Maier & Neustadt, P.C.

[57] ABSTRACT

There is provided a water-absorptive composite comprising a fibrous substrate bearing water-absorptive polymer particles. A process for producing the water-absorptive composite comprises the steps of: allowing an aqueous monomer solution containing a polymerizable monomer capable of providing a water-absorptive polymer to initiate polymerization by the use of a redox polymerization initiator; applying the resultant reaction mixture, which is in the course of polymerization, dropwise onto a fibrous substrate; and allowing the polymerization to proceed and finish on the substrate.

4 Claims, 1 Drawing Sheet

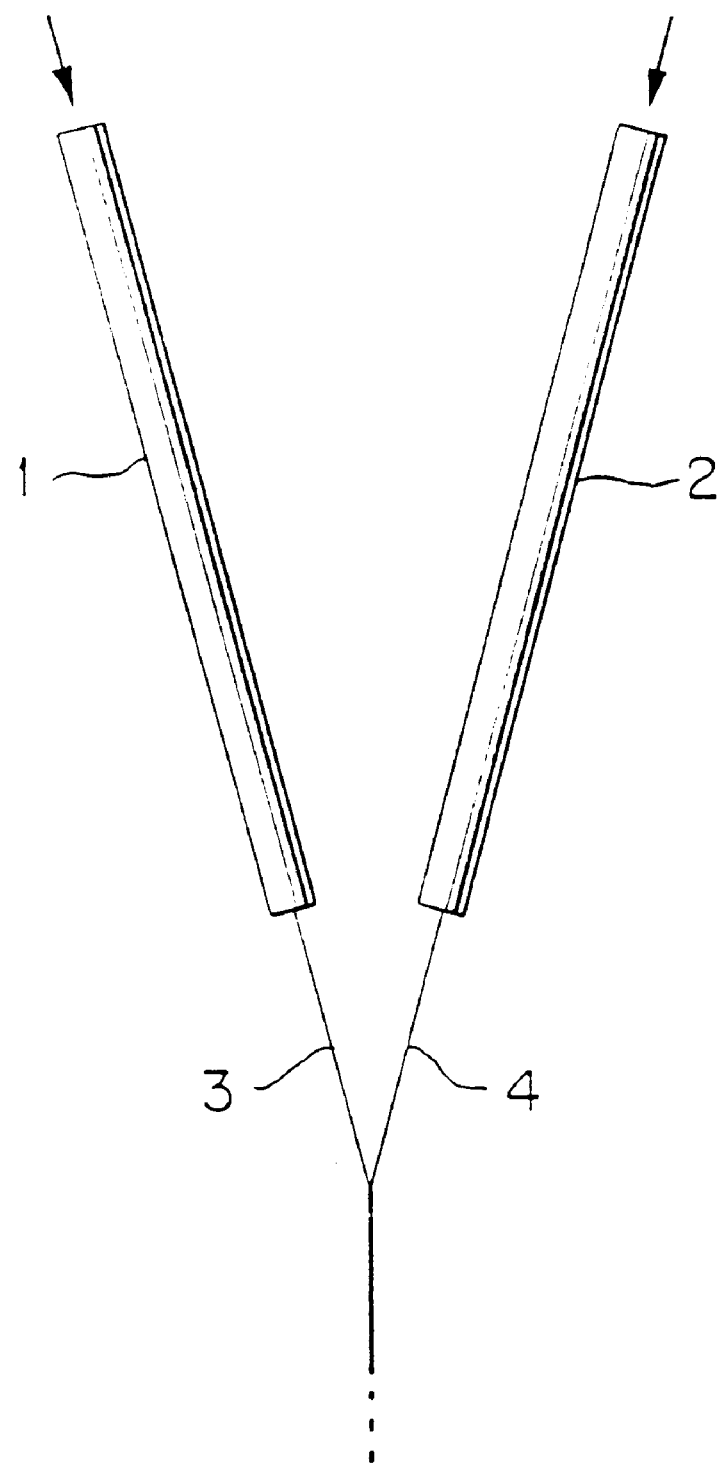
F I G. 1

WATER-ABSORPTIVE COMPOSITE AND PROCESS FOR PRODUCING THE SAME

This application is a Division of application Ser. No. 08/665,416, filed on Jun. 18, 1996, now abandoned.

BACKGROUND OF THE INVENTION

1. Field of the Invention

The present invention relates to a water-absorptive composite and a process for producing the same. More particularly, the present invention relates to a water-absorptive composite exhibiting excellent water absorption capacity and a high rate of water absorption, having a low content of unpolymerized monomer, and containing highly water-absorptive polymer particles stably fixed to a fibrous substrate, and a process for producing the same.

2. Background Art

Paper, pulp, nonwoven fabrics, spongy urethane resin and the like have hitherto been used as water-retaining materials in various sanitary goods, including sanitary napkins and disposable paper diapers, as well as in various materials for agriculture. The water absorption capacity of these materials is as low as about 10 to 50 times their own weight, making it necessary to use these materials in a large amount for absorbing or retaining a large amount of water. Therefore, the above materials are very bulky, and pressing of the materials with water absorbed therein, unfavorably causes water to be readily released from the materials.

To overcome the drawbacks of the above type of water-absorptive materials, a variety of highly water-absorptive polymer materials have been proposed. For example, a graft polymer of starch (for example, Japanese Patent Publication No. 46199/1978), modified cellulose (for example, Japanese Patent Laid-Open No. 80376/1975), and crosslinked water-soluble polymers (for example, Japanese Patent Publication No. 23462/1968), and self-crosslinking polymers of alkali metal salts of acrylic acid (for example, Japanese Patent Publication No. 30710/1979).

These highly water-absorptive polymer materials have solved the above problems in their own ways and have water-absorptive properties on a considerably high level. Since, however, they are, in most cases, prepared in a powder form, the use thereof for sanitary goods, such as sanitary napkins and paper diapers, necessitates for the materials to be homogeneously dispersed on a substrate, such as tissue paper, nonwoven fabric, or cotton. The polymer powder dispersed in this way, however, cannot be stably fixed to the substrate without difficulty, and, in many cases, the polymer powder dispersed becomes to be locally agglomerated. Further, the swollen gel after water absorption cannot be stably fixed to the substrate and is readily moved from the substrate. For this reason, an absorbent article, for example, a paper diaper feels coarse and stiff after urination, creating a very uncomfortable feel for a wearer. Moreover, the above method of dispersing a powdery polymer on a substrate to prepare an absorbent article involves problems such as troublesome handling of the powder and operational difficulties in carrying out homogeneous dispersion in an efficient manner.

Japanese Patent Publication No. 67712/1991 proposes, as one method for solving the above problems, a process for producing a water-absorptive composite, comprising the steps of: applying an aqueous acrylic monomer solution in a predetermined pattern onto a formed fibrous substrate; irradiating an electromagnetic radiation or a corpuscular ionizing radiation to the substrate with the acrylic monomer solution applied thereon to convert the acrylic monomer to a highly water-absorptive polymer. According to this method, a considerable improvement in homogeneous dispersion of the polymer and stable fixation of the polymer onto the substrate is attained. Since, however, the electromagnetic radiation or corpuscular ionizing radiation is used in the conversion of the monomer to a highly water-absorptive polymer, the polymer is very likely to undergo excessive self-crosslinking, unfavorably resulting in a composite having very poor properties for absorbent articles, particularly very poor water absorption capacity which is less than half of the water absorption capacity of a composite prepared by the above method of using powdery highly water-absorptive polymer.

Japanese Patent Laid-Open No. 149609/1985 proposes a process for producing a water-absorptive composite, comprising the steps of: previously impregnating a water-absorptive organic material with an aqueous acrylate monomer solution; and adding an atomized water-soluble radical polymerization initiator or water-soluble reducing agent to polymerize the acrylate monomer. According to this process, since the water-soluble polymerization initiator is added after the impregnation of the water-absorptive organic material with the acrylate monomer, the polymerization initiator, even when added in an atomized state, reaches as droplets the monomer layer, causing "uneven polymerization", that is, a difference in degree of polymerization of the acrylic acid monomer due to a difference in concentration of the polymerization initiator on the monomer layer. Therefore, it is very difficult to completely polymerize the monomer, leaving a large amount of the monomer unreacted, which is undesirable also in the light of safety problem. Further, since the water-absorptive organic material substrate is previously impregnated with the aqueous acrylate monomer solution, the aqueous monomer solution penetrates into the inside of the substrate and is polymerized there, which would reduce the diameter of capillaries as formed between the fibers. This would lead to a lowered rate of water absorption of the resultant composite and a poor swelling of the resultant polymer upon its water absorption.

Further, Japanese Patent Laid-Open No. 11675/1989 discloses a process for producing a water-absorptive composite comprising a water-absorptive acrylic polymer and a fibrous substrate, characterized by comprising the steps of: discontinuously coating a liquid comprising a mixture of a hydrophilic acrylic monomer with a hydrophilic acrylic polymer onto a fibrous substrate; and then polymerizing the liquid. In this process, however, there is a limitation on the shape and size of discontinuously formed polymer areas. In particular, it is very difficult to form fine polymer areas. This would provide a composite with insufficient water absorption properties.

Japanese Patent Publication No. 58030/1993 has proposed an absorbent article comprising a fibrous substrate and a water-absorptive polymer discontinuously adhered to the substrate, wherein at least part of the water-absorptive polymer spherically envelops the substrate. This absorbent article may overcome to some degree the drawbacks in the above mentioned conventional products.

The present inventors, however, have found that this absorbent article also has some problems. Specifically, the adhesion of the water-absorptive polymer to the substrate is unsatisfactory when the polymer is swollen upon water absorption, so that the polymer is likely to come off from the substrate. Further, despite the intended use as water-absorptive articles, the use of a hydrophilic fibrous substrate is not considered suitable. Thus, this article is taught to be prepared by spraying an aqueous monomer solution onto a substrate. Since the catalyst incorporated in the aqueous monomer solution is not of a redox type but a simple peroxide catalyst, the polymerization is slowly initiated. Therefore, when droplets of the Aqueous monomer solution reach the substrate, the viscosity thereof is still low. In order that such a low-viscosity monomer solution can successfully grow into a polymer which envelops spherically the substrate, the substrate should be non-hydrophilic so as not to cause absorption or impregnation of the aqueous low-viscosity monomer solution (as described in the above publication, the occurrence of this phenomenon will result in the formation of a "web-like" water-absorptive polymer).

An object of the present invention is to provide a water-absorptive composite comprising a fibrous substrate bearing water-absorptive polymer particles, which contains few residual monomers, exhibits excellent water absorption capacity and a high rate of water absorption and in which the highly water-absorptive polymer particles are stably fixed to the fibrous substrate.

Another object of the present invention is to provide a process for producing the above water-absorptive composite, which overcomes the above drawbacks in the prior art, enables a highly water-absorptive polymer to be fixed in any form and pattern onto any formed fibrous substrate, and can produce the water-absorptive composite in a simple manner at a low cost.

SUMMARY OF THE INVENTION

It has now been found by the present inventors that a water-absorptive composite which has excellent water absorption properties and contains few residual monomers, and in which water-absorptive polymer particles are stably fixed in a desired form and pattern onto a fibrous substrate, can be prepared in a simple manner at a low cost by a process which comprises initiating polymerization of a monomer by the use of a redox initiator, applying the resultant reacting mixture, which is in the course of polymerization, dropwise onto a fibrous substrate and allowing the polymerization to proceed on the substrate.

Thus, the present invention, In one aspect thereof, provides a water-absorptive composite comprising a fibrous substrate bearing water-absorptive polymer particles, the water-absorptive composite having the following physical characteristics (1) to (4):

(1) the porosity of the substrate of 50 to 99.5%;
(2) the primary particle diameter of the polymer particles of 50 to 1000 $\mu$m;
(3) the amount of the polymer particles of 10 to 500 g per $m^2$ of the substrate; and
(4) the percentage retention (A) of the polymer particles, defined by the following equation, of not less than 60%:

$$A(\%) = \frac{W_0 - w}{W_0} \times 100$$

wherein $W_0$ represents the dry weight (g) of a water-absorptive polymer in the following sample and w represents the dry weight (g) of a water-absorptive polymer fallen from the sample,
w being measured by a method wherein physiological saline is absorbed into a sheet sample, having a size of 60 mm×300 mm and a thickness of 0.5 to 20 mm, of a water-absorptive composite until the absorption reaches the saturation, the sample is then put on a stone table; an iron roller with a smooth surface, having a diameter of 105 mm, a width of 60 mm and a weight of 4 kg, is reciprocated on the sample five times at a speed of 10 cm/sec, and the weight, after drying, of a water-absorptive polymer fallen from the sample is measured as the w value.

The present invention, in another aspect thereof, provides a process for producing the above water-absorptive composite, comprising the steps of: allowing an aqueous monomer solution containing a polymerizable monomer capable of providing a water-absorptive polymer to initiate polymerization by the use of a redox polymerization initiator; applying the resultant reaction mixture, which is in the course of polymerization, dropwise onto a fibrous substrate; and allowing the polymerization to proceed and finish on the substrate.

According to the present invention, a water-absorptive article not entailing the above drawbacks of the prior art can be obtained. In particular, when droplets of an aqueous monomer solution are formed in a gas phase and, in addition, the polymerization of the monomer is initiated by the use of a redox initiator, the viscosity of the droplets on arriving at a fibrous substrate is much higher than that of the aqueous monomer solution. Therefore, the absorption of impregnation of the droplets in the substrate is less likely to occur even when the substrate is constituted by a hydrophilic fiber. Further, according to the water-absorptive composite of the present invention, the water-absorptive polymer particles on the substrate, even when they are in a swollen state, are less likely to come off from the substrate.

BRIEF DESCRIPTION OF THE DRAWING

FIG. 1 is a diagram showing one embodiment of a nozzle structure to be used for practicing the process for producing a water-absorptive composite according to the present invention. In the drawing, numeral 1 denotes a nozzle for a first liquid, numeral 2 a nozzle for a second liquid, numeral 3 a first liquid, and numeral 4 a second liquid.

DETAILED DESCRIPTION OF THE INVENTION

Production of Water-Absorptive Composite
<Polymerizable Monomer>

The polymerizable monomer used in the present invention is not particularly limited so far as it provides a water-absorptive polymer and the polymerization of the monomer can be initiated with the use of a redox initiator. Since the monomer is used as an aqueous solution, it should be soluble in water. Monomers, capable of providing water-absorptive polymers are generally soluble in water.

Organic unsaturated carboxylic acids or salts thereof are representative of such monomers and preferably used in the present invention. Specific examples thereof include acrylic acid or salts thereof, methacrylic acid or salts thereof, maleic acid or salts thereof, and itaconic acid or salts thereof. They may be used singly on as a mixture of two or more of monomers belonging to the same group or different groups.

Among the above monomers, acrylic acid or salts thereof and methacrylic acid or salts thereof are preferred with acrylic acid or salts thereof being particularly preferred.

As described above, the polymerizable monomer which provides a water-absorptive polymer in the present invention is preferably an organic unsaturated carboxylic acid or a salt thereof, and a preferred aqueous monomer solution contains a monomer composed mainly of the organic unsaturated carboxylic acid or a salt thereof. The expression "composed mainly of an organic unsaturated carboxylic acid or a salt thereof" used herein means that the organic unsaturated carboxylic acid or a salt thereof is used in an amount of not less than 50% by mole, preferably not less than 80% by mole, based on the total amount of the polymerizable monomer.

The salt of the organic unsaturated carboxylic acid is usually a water-soluble salt, and typical examples thereof include an alkali metal salt, an alkaline earth metal salt, and an ammonium salt. The degree of neutralization is suitably determined according to the intended purposes. In the case of acrylic acid it is generally preferred that 20 to 90% by mole of the carboxyl groups have been neutralized with an alkali metal salt or an ammonium salt. When the degree of partial neutralization of the acrylic acid monomer is less than 20% by mole, the water absorption capacity of the resultant polymer is likely to be deteriorated.

Hydroxides or bicarbonates of alkali metals and ammonium hydroxide are usable for the neutralization of an acrylic acid monomer. Alkali metal hydroxides are preferred, and specific examples thereof include sodium hydroxide and potassium hydroxide.

In the present invention, besides the above organic unsaturated carboxylic acids, monomers copolymerizable with them, for example, (meth)acrylamide, (poly)ethylene glycol (meth)acrylate, and 2-hydroxyethyl (meth)acrylate, and alkyl esters of acrylic acid, although they are monomers of a low water solubility, such as methyl acrylate and ethyl acrylate, may also be copolymerized in such an amount as will not be detrimental to the properties of the resultant water-absorptive resin. The term "(meth)acryl" used herein is intended to mean both "acryl" and "methacryl."

In this connection, it is needless to say that among the above monomers, those capable of providing water-absorptive polymers by themselves can be used as a main monomer in the "aqueous solution of a polymerizable monomer capable of providing a water-absorptive polymer" rather than an auxiliary component for the organic unsaturated carboxylic acid or a salt thereof.

Though the organic unsaturated carboxylic acid or a salt thereof, particularly acrylic acid or a salt thereof, may more or less undergo self-crosslinking to form a self-crosslinked polymer, it is preferred to use a crosslinking agent to positively form a crosslinking structure. In general, the use of a crosslinking agent results in improved water-absorptive properties of the resultant water-absorptive polymer. Preferred crosslinking agents include divinyl compounds copolymerizable with the above monomers, for example, N,N'-methylenebis(meth)acrylamide and (poly)ethylene glycol di(meth)acrylate, and water-soluble compounds having two or more functional groups reactive with carboxylic acid, for example, polyglycidyl ethers, such as ethylene glycol diglycidyl ether and polyethylene glycol diglycidyl ether. Among them, N,N'-methylenebis(meth)acrylamide is particularly preferred. The amount of the crosslinking agent used is generally 0.001 to 1% by weight, preferably 0.01 to 0.5% by weight, based on the amount of the monomer charged.

The concentration of the polymerizable monomer in the aqueous monomer solution containing an organic unsaturated carboxylic or a salt thereof as the main component is generally not less than 20% by weight, preferably not less than 25% by weight. When the concentration is less than 20% by weight, the water absorption capacity of the water-absorptive resin, after the polymerization, is like to be poor. The upper limit of the concentration is generally about 80% by weight.

<Redox Polymerization Initiator>

The polymerization initiator used in the present invention is one which can form a redox system comprising a combination of an oxidizing radical initiator with a reducing agent, and it should be soluble in water to some extent. Such oxidizing agents include peroxides, for example, hydrogen peroxide, persulfates such as ammonium persulfate and potassium persulfate, hydroperoxides such as t-butyl hydroperoxide and cumene hydroperoxide; and other oxidizing agents, such as secondary cerium salts, permanganates, chlorites, and hypochlorites. Among them, hydrogen peroxide is particularly preferred. The amount of the oxidizing agent used is generally 0.01 to 10% by weight, preferably 0.1 to 2% by weight, based on the polymerizable monomer.

The reducing agent, which can form a redox system with the oxidizing agent, may include sulfites such as sodium sulfite and sodium hydrogensulfite, sodium thiosulfate, cobalt acetate, copper sulfate, ferrous sulfate, L-ascorbic acid, and alkali metal salts of L-ascorbic acid. Among them, L-ascorbic acid and alkali metal salts of L-ascorbic acid are particularly preferred. The amount of the reducing agent used is generally 0.001 to 10% by weight, preferably 0.01 to 2% by weight, based on the polymerizable monomer.

<Polymerization Method>

According to the present invention, a redox polymerization initiator is supplied to an aqueous solution of a monomer capable of providing a water-absorptive polymer, preferably an aqueous solution of a polymerizable monomer composed mainly of an organic unsaturated carboxylic acid or a salt thereof to initiate the polymerization of the monomer. The resultant mixture, which is in the course of polymerization and contains the monomer and the polymer formed, is applied dropwise onto a fibrous substrate, and the polymerization is allowed to proceed and finish on the substrate.

In the above polymerization method, careful consideration should be given to the fact that the polymerization is immediately initiated upon the formation of a redox system in the presence of the monomer, and, since the polymerization initiated with a redox initiator is a chain polymerization, it reaches a certain degree of polymerization in a relatively short time, that is, the time taken for the viscosity of the aqueous monomer solution to reach a certain level is relatively short. In this situation, operation conditions should be properly selected so that the aqueous monomer solution after the initiation of polymerization is fed as droplets of a predetermined viscosity onto the substrate.

One preferred method, in consideration of the above, is to mix a first liquid, comprising aqueous polymerizable monomer solution containing either one of an oxidizing agent and a reducing agent, which will together constitute a redox polymerization initiator, with a second liquid, comprising an aqueous solution containing an oxidizing agent or a reducing agent, which is the other agent not contained in the first liquid, and optionally a polymerizable monomer, in a gas phase to initiate the polymerization.

Specific methods for mixing the two liquids include one wherein the first and second liquids are ejected from different nozzles so that the angle between the direction of flow of the first liquid and the direction of flow of the second liquid is not less than 15°, and the two liquids collide against each other both in the form of a liquid column. This method, wherein the two liquids are allowed to collide against each other at the above specified angle, can utilize part of the energy of flowing liquids in the mixing. The cross angle between the first and second liquids ejected from the respective nozzles may be suitably determined according to the nature of the polymerizable monomer, the flow rate ratio and the like. For example, the angle may be made small when the linear velocity of the liquids is high. In general, an angle of not less than 15° is necessary for attaining satisfactory mixing, with an angle of not less than 20° being preferred. The upper limit of the angle is not particularly limited so far as a liquid column is formed after collision of the first liquid against the second liquid (as described in detail below). In the case of industrial apparatuses, however, the angle is preferably not more than 120°, particularly preferably not more than 100°.

In this method, the first and second liquids, ejected from the respective nozzles, both should be in the form of a liquid column when they collide against each other. This permits the liquids to be mixed together in a predetermined flow rate ratio, thus assuring the intended polymerization. When these liquids, in a droplet form, are allowed to collide with each other, the mixing ratio is liable to be different from the initial flow rate ratio. The distance between the front ends of the nozzles may be freely set, and, as the case may be, the front ends of the nozzles can be in contact with each other, so far as the fluids, both in the form of a liquid column can be allowed to collide against each other. The inner diameter of the nozzle may be suitably selected according to the nature of the polymerizable monomer used and the form of the contemplated water-absorptive composite. It, however, is preferably 0.05 to 2.0 mm, more preferably 0.1 to 1.0 mm.

The temperature of the first liquid is generally from room temperature to about 60° C., preferably from room temperature to about 40° C., and the temperature of the second liquid also is generally from room temperature to about 60° C., preferably from room temperature to about 40° C.

As stated above, the aqueous solutions ejected from the nozzles, respectively in the form of a liquid column, are allowed to collide against each other, thus combining the two liquids. After that, a liquid column is formed and held in this state for a certain period of time. Thereafter, the liquid column is broken into droplets which are then dropped onto a substrate.

The time taken for the liquid column to be held after the collision of the two liquids, the length of the liquid column, and the size of the droplets may vary depending upon preset conditions, such as the inner diameter of the nozzles. In general, however, the holding time is 0.1 to 3 seconds, the length of the liquid column is 3 to 50 mm, and the size of the droplets is 5 to 3000 μm in terms of the diameter.

Preferred gases usable for constituting the gas phase, which provides a place for the initiation of polymerization and the formation of droplets in the course of polymerization, include gasses inert to the polymerization, such as nitrogen, helium, and carbonic acid gas. Air also is usable. The humidity of the gas is not particularly limited. The gas temperature is from room temperature up to 150° C., preferably up to 100° C. The direction of flow of the gas may be either counter flow or parallel flow relative to the direction of advance of the liquid column and the droplets. However, when the residence time of the droplets in the gas phase should be increased, that is, when the degree of polymerization of the polymerizable monomer should be increased (as described in detail below) so as to enhance the viscosity of the droplets, the counter flow (direction opposite to the gravity) is preferred.

Various conditions are to be set so that the degree of polymerization when the droplets reach the substrate can be 3 to 90%, preferably 3 to 80%, more preferably 5 to 70%. When the degree of polymerization is too low, the liquid dropped onto the substrate may spread over or absorbed or impregnated into the substrate, making it impossible to fix the liquid onto the substrate in any form and pattern, for example, in a dot pattern. On the other hand, when it is too high, the adhesion of the liquid to the substrate is very weak and the resultant water-absorptive polymer is poorly fixed to the substrate.

The water-absorptive polymer formed by the polymerization can be fixed in any desired form and pattern on the substrate by properly varying the diameter and angle of the nozzles, the kind and amount of the polymerization initiator, the distance between the nozzles and the substrate, the temperature of the gas phase and the like, by using a plurality of sets of nozzles in a suitable arrangement, or by varying with time the relative position or distance between the nozzles and the substrate. From the viewpoint of water absorption properties, it is preferred that the water-absorptive polymer be fixed on the substrate in such a manner that the polymer particles are each independently fixed in a dot form on the substrate. Depending upon specific applications, however, the polymer particles may also be continuously fixed in a line pattern or wholly on the substrate. The nozzles to be used are not limited to the above described two facing nozzles. Use may also be made of, for example, a band of two nozzles with the front ends aligned with each other and a double nozzle comprising two nozzles with one inserted in the other.

As described above, the polymerization starts after the collision of the two liquids both in the form of a liquid column and proceeds while the mixed liquid drops down to the substrate, and further proceeds and finish on the substrate. During the polymerization, if desired, a heating treatment or irradiation of ultraviolet light or electron beam may be carried out to promote part or the whole of the polymerization. When the polymerization is completed, the residual monomer content is generally not more than 2000 ppm, preferably not more than 1000 ppm.

Surface-crosslinking of the polymer on the substrate with a crosslinking agent may also be carried out so as to enhance the water absorption capacity.

<Fibrous Substrate>

The fibrous substrate to which the reaction mixture in the course of polymerization is applied is preferably a "formed" fibrous substrate. Specific examples of formed fibrous substrates include those having particular shapes, for example, pads, carded or air-laid webs, tissue paper, woven fabrics such as cotton gauze, knit cloth and nonwoven fabrics. The "formed fibrous substrate" may be cut, joined, or shaped to make it fit for a final article, but it is no longer subjected to a further web-forming process.

Since the substrate is used for water-absorptive articles, preferred fibers for constituting the substrate include hydrophilic fibers, such as wood pulp, rayon, cotton, regenerated cellulose and other cellulosic fibers. They can best enjoy the benefit of the present invention. A substrate composed mainly of the above hydrophilic fiber is thus particularly preferred in the present invention. However, a substrate composed mainly of a polyester fiber is also preferably used. It is also possible to use fibrous substrates composed mainly of other non-hydrophilic fibers, for example, polyethylene, polypropylene, polystyrene, polyamide, polyvinyl alcohol, polyvinyl chloride, polyvinylidene chloride, polyacrylonitrile, polyurea, polyurethane, polyfluoroethylene, and polyvinylidene cyanide fibers.

In the above described specific method of preparing the water-absorptive composite according to the present invention, the porosity of the fibrous substrate used is an important factor. Specifically, in the present invention, the porosity of the fibrous substrate should be 50 to 99.5%. When the porosity is less than 50%, the adhesion of the polymer particles to the substrate is poor. Further, in this case, the substrate is unfavorably stiff. On the other hand, when the porosity is larger than 99.5%, the retention of the polymer particles on the substrate is insufficient. Moreover, the strength of the substrate is unsatisfactory.

The porosity of the substrate is calculated by the following equation.

Porosity of substrate (%)=[(weight of substrate (g))/(area of substrate (cm$^2$)×thickness (cm)×true specific gravity (g/cm$^3$))]×100 (%)

The "formed" fibrous substrate is usually in the shape of a cloth or a sheet. Accordingly, the thickness of the substrate is usually about 0.5 to 20 mm, and the weight of the substrate per unit area is usually about 10 to 500 g/m$^2$.

<Production of Water-Absorptive Composite>

An example of an actual process for producing a water-absorptive composite is as follows. The above substrate sheet is carried by means of a belt conveyor, while a reaction mixture, which is in the course of the polymerization of the aqueous polymerizable monomer solution, is applied dropwise onto the substrate sheet in the above described manner. The polymerization of the reaction mixture on the substrate is allowed to proceed for a period of time to complete the polymerization. Since the water-absorptive polymer thus obtained contains water, it is dried to remove water, thereby preparing a water-absorptive composite sheet which may then be cut into a predetermined shape and size to fit it for a final article.

Water-Absorptive Composite

The structure of the water-absorptive composite thus obtained should be such that the polymer is fixed in a particulate form on the substrate. The amount of the highly water-absorptive polymer borne on the substrate should be 10 to 500 g/m$^2$. When the amount is smaller than 10 g/m$^2$, the water absorption properties are unsatisfactory, while when it exceeds 500 g/m$^2$, the sheet feels coarse and stiff, which is unfavorable especially for use in sanitary goods.

The diameter of the water-absorptive polymer particles is about 50 to 1000 μm. When the particle diameter exceeds 1000 μm, the polymer cannot fully exhibit its water absorption capacity. On the other hand, when it is less than about 50 μm, the adhesion of the water-absorptive particles to the substrate is insufficient.

The average particle diameter of the water-absorptive polymer particles borne on the water-absorptive composite is determined by observing the composite under a microscope. Specifically, the number and diameter of water-absorptive polymer particles within the range of a microscope are read, and the average particle diameter is calculated by the following equation.

The average particle diameter (μm)=(total of diameter of individual polymer particles)/(number of polymer particles)

According to the water-absorptive composite of the present invention, the polymer particles are borne on the fibrous substrate without deteriorating the texture inherent in the fibrous substrate used, for example, the flexibility. Further, the water-absorptive polymer particles are firmly fixed on the fibrous substrate. In particular, even the gel after water absorption is hard to be released from the fibrous substrate.

The degree of adhesion or fixation of the polymer particles onto the substrate in the water-absorptive composite can be determined by percentage retention (A) defined by the following equation:

$$A(\%) = \frac{W_0 - w}{W_0} \times 100$$

wherein $W_0$ represents the dry weight (g) of a water-absorptive polymer in the following sample, and w represents the dry weight (g) of a water-absorptive polymer fallen from the sample, w being measured by a method wherein physiological saline is absorbed into a sheet sample, having a size of 60 mm×300 mm and a thickness of 0.5 to 20 mm, of a water-absorptive composite until the absorption reaches the saturation, the sample is then put on a stone table; an iron roller having a diameter of 105 mm, a width of 60 mm and a weight of 4 kg is reciprocated on the sample five times at a speed of 10 cm/sec, and the weight, after drying, of a water-absorptive polymer fallen from the sample is measured as the w value. The water-absorptive composite of the present invention has the above-defined percentage retention (A) of not less than 60%.

According to the water-absorptive composite of the present invention, the water-absorptive polymer, also in the dry state, shows high adhesion or fixation onto the substrate. Thus, the percentage retention (A') of the polymer particles, defined by the following equation, is not less than 90%:

$$A'(\%) = \frac{W'_0 - w'}{W'_0} \times 100$$

wherein $W_0'$ represents the weight (g) of a water-absorptive polymer in the following sample, and w' represents the weight (g) of a water-absorptive polymer fallen from the sample, w' being measured by a method wherein a sheet sample, having a size of 60 mm×300 mm and a thickness of 0.5 to 20 mm, of a water-absorptive composite is put on a stone table; an iron roller having a diameter of 105 mm, a width of 60 mm and a weight of 4 kg is reciprocated on the sample ten times at a speed of 10 cm/sec, and the weight of a water-absorptive polymer fallen from the sample is measured as the w' value.

The water-absorptive composite according to the present invention is excellent also in the water absorption capacity and rate of water absorption, which can be determined by the equation shown below. As is apparent from the equation, the water absorptive capacity and the rate of water absorption are to be determined for water-absorptive polymers as borne on the substrate.

According to the present invention, the water absorption capacity is generally not less than 20 (times), usually 30 (times) or more, and often over 35 (times).

The rate of water absorption is generally not less than 15 g/5 min, usually 20 g/5 min or more, and often over 25 g/5 min.

The water-absorptive composite of the present invention has the further advantage that the amount of the residual unreacted monomer is small. According to the present invention, the concentration of the residual unreacted monomer, which can be measured by the below described method, is generally not more than 500 ppm, usually not more than 300 ppm, and often not more than 100 ppm.

(1) Physiological Saline Absorption Capacity

About 1.0 g of a water-absorptive composite and about 200 g of physiological saline having a concentration of 0.9% by weight are weighed and placed in a 300-ml beaker, and the beaker is allowed to stand for about 4 hours, thereby permitting the polymer to be adequately swollen with the physiological saline. The water-absorptive composite is then put on a 100-mesh sieve to drain. The physiological saline absorption capacity is calculated by the following equation:

Physiological saline absorption capacity=[(weight of water-absorptive composite after water absorption (g))−(weight of substrate alone after water absorption (g))]/(weight of water-absorptive polymer particles borne on water-absorptive composite (g))

(2) Rate of Water Absorption

About 200 g of physiological saline having a concentration of 0.9% by weight is weighed and placed in a 300-ml beaker, and then about 1.0 g of a water-absorptive composite is weighed and added to the physiological saline. 5 minutes after the addition of the water-absorptive composite, the water-absorptive composite is put on a 100-mesh sieve to drain. The amount of the physiological saline thus drained off is weighed, and the physiological saline absorption capacity is determined according to the above equation, and the value thus determined is regarded as the rate of water absorption.

(3) Residual Unreacted Polymerizable Monomer Concentration 0.5 g of a water-absorptive composite is accurately weighed and added to 1 liter of ion-exchanged water in a 2-liter beaker, and the contents of the beaker is stirred for about 10 hours so as to allow the composite to be adequately swollen with water. The polymer gel after swelling is subjected to filtration through a 200-mesh sieve. The filtrate is analyzed by high performance liquid chromatography. Separately, standard monomer solutions having known concentrations are prepared, and a calibration curve is prepared using the solutions. The absolute concentration of the residual unreacted monomer can be determined based on the calibration curve.

The following examples and comparative examples further illustrate the present invention but are not intended to limit it. In the following examples, the physiological saline absorption capacity, the rate of water absorption, the amount of the residual unreacted polymerizable monomer, and the adhesion of the water-absorptive polymer to the fibrous substrate before and after water absorption (percentage retention A' and percentage retention A) are measured by the above methods.

EXAMPLE 1

57.3 parts by weight of a 48.5 wt % aqueous sodium hydroxide solution, 6.4 parts by weight of water, 0.15 part by weight of a crosslinking agent (N,N'-methylenebisacrylamide), and 5.0 parts by weight of a 30 wt % aqueous hydrogen peroxide solution as an oxidizing agent were added to 125 parts by weight of an 80 wt % aqueous acrylic acid solution to prepare a solution A. The solution A had a monomer concentration of 60% by weight and a degree of neutralization of 50% by mole.

Separately, 57.3 parts by weight of a 48.5 wt % aqueous sodium hydroxide solution, 9.9 parts by weight of water, 0.15 part by weight of a crosslinking agent (N,N'-methylenebisacrylamide), and 1.5 parts by weight of L-ascorbic acid as a reducing agent were added to 125 parts by weight of an 80 wt % aqueous acrylic acid solution to prepare a solution B. The solution B had the same monomer concentration and degree of neutralization as the solution A.

Two nozzles, with the structure shown in FIG. 1, having an inner diameter of 0.13 mm were provided. The angle between the nozzles was set at 30° with the distance between the front ends of the nozzles set at 4 mm. The solution A and the solution B each were heated to 40° C., and respectively pumped into and ejected through the nozzles 1 and 2 as the solutions 3 and 4 both at a flow rate of 5 m/sec.

Immediately after ejection from the nozzles, the solutions A and B meet to form a liquid column, having a length of about 10 mm, which then changed into droplets and dropped in an ascending air current (60° C.). The droplets were received by a nonwoven fabric of polypropylene/polyethylene (porosity 98%, weight per unit area 100 g/m$^2$) provided 100 cm below the front ends of the nozzles, and dried until the water content of the water-absorptive polymer borne on the nonwoven fabric reached 5%, thereby preparing a water-absorptive composite A with the amount of the polymer borne on the nonwoven fabric being 200 g/m$^2$. The results are shown in Table 1.

EXAMPLE 2

A water-absorptive composite B was prepared in the same manner as in Example 1, except that the solution A was prepared by adding 80.4 parts by weight of a 48.5 wt % aqueous sodium hydroxide solution, 2.0 parts by weight of water, 0.15 part by weight of a crosslinking agent (N,N'-methylenebisacrylamide), and 5.0 parts by weight of a 30 wt % aqueous hydrogen peroxide solution as an oxidizing agent to 125 parts by weight of an 80 wt % aqueous acrylic acid solution, and the solution B was prepared by adding 80.4 parts by weight of a 48.5 wt % aqueous potassium hydroxide solution, 5.5 parts by weight of water, 0.15 part by weight of a crosslinking agent (N,N'-methylenebisacrylamide), and 1.5 parts by weight of L-ascorbic acid as a reducing agent to 125 parts by weight of an 80 wt % aqueous acrylic acid solution. The results are shown in Table 1.

EXAMPLE 3

A water-absorptive composite C was prepared in the same manner as in Example 1, except that a nonwoven fabric of polyester (porosity 95%, weight per unit area 100 g/m$^2$) was used instead of the nonwoven fabric of polypropylene/polyethylene (porosity 98%, weight per unit area 100 g/m$^2$). The results are shown in Table 1.

EXAMPLE 4

A water-absorptive composite D was prepared in the same manner as in Example 1, except that a nonwoven fabric of rayon (porosity 90%, weight per unit area 100 g/m$^2$) was used instead of the nonwoven fabric of polypropylene/polyethylene (porosity 98%, weight per unit area 100 g/m$^2$). The results are shown in Table 1.

EXAMPLE 5

The water-absorptive composite A prepared in Example 1 was irradiated with ultraviolet light at 1000 mJ/cm$^2$ to prepare a water-absorptive composite E. The results are shown in Table 1.

EXAMPLE 6

In this example, the solutions A and B prepared in Example 1 were used. Two nozzles, with the structure shown in FIG. 1, having an inner diameter of 0.20 mm were provided. The angle between the nozzles was set at 30° with the distance between the front ends of the nozzles set at 4 mm. The solution A and the solution B each were heated to 40° C., and respectively pumped into and ejected through the nozzles 1 and 2 as the solutions 3 and 4 both at a flow rate of 5 m/sec.

Immediately after ejection from the nozzles, the solutions A and B meet to form a liquid column, having a length of about 20 mm, which then changed into droplets and dropped in a nitrogen atmosphere (70° C.). The droplets were received by a nonwoven fabric of polypropylene/ polyethylene (porosity 98%, weight per unit area 100 g/m$^2$) provided 30 cm below the front ends of the nozzles, while the nonwoven fabric was allowed to move transversely so that the resultant water-absorptive polymer particles formed a lattice pattern having a line width of 2 mm and a line interval of 5 mm on the nonwoven fabric substrate. Thereafter, the nonwoven fabric was dried until the water content of the water-absorptive polymer reached 5%, thereby preparing a water-absorptive composite F with the amount of the polymer borne on the nonwoven fabric being 200 g/m$^2$. The results are shown in Table 1.

EXAMPLE 7

A water-absorptive composite G was prepared in the same manner as in Example 1, except that the solution A was prepared by adding 27.4 parts by weight of maleic anhydride, 68.9 parts by weight of a 48.5 wt % aqueous sodium hydroxide solution, 18.0 parts by weight of water, 0.15 part by weight of a crosslinking agent (N,N'-methylenebisacrylamide), and 5.0 parts by weight of a 30 wt % aqueous hydrogen peroxide solution as an oxidizing agent to 100 parts by weight of an 80 wt % aqueous acrylic acid solution, and the solution B was prepared by adding 27.4l parts by weight of maleic anhydride, 68.9 parts by weight of a 48.5 wt % aqueous sodium hydroxide solution, 21.5 parts by weight of water, 0.15 part by weight of a crosslinking agent (N,N'-methylenebisacrylamide), and 1.5 parts by weight of L-ascorbic acid as a reducing agent to 100 parts by weight of an 80 wt % aqueous acrylic acid solution. The results are shown in Table 1.

COMPARATIVE EXAMPLE 1

The solution A prepared in Example 1 was heated to 40° C. and pumped into a nozzle having an inner diameter of 0.13 mm at a flow rate of 5 m/sec.

Immediately after ejection from the front end of the nozzle, the solutions A formed a liquid column, which then changed into droplets and dropped in an ascending air current (60° C.). The droplets were received by a nonwoven fabric of polypropylene/polyethylene (porosity 98%, weight per unit area 100 g/m$^2$) provided 100 cm below the front end of the nozzle. Further, the solution B prepared in Example 1 was applied onto the above nonwoven fabric in the same manner as described above in connection with the solution A.

The solutions A and B reacted with each other on the substrate, and the polymerization proceeded on the substrate to give a water-absorptive polymer. The polymer was dried to a water content of 5% to obtain a water-absorptive composite H with the amount of the polymer borne on the nonwoven fabric being 200 g/m$^2$. The results are shown in Table 1.

COMPARATIVE EXAMPLE 2

A water-absorptive composite I was prepared in the same manner as in Example 1, except that the nonwoven fabric of polypropylene/polyethylene was provided 800 cm below the front ends of the nozzles. The results are shown in Table 1.

COMPARATIVE EXAMPLE 3

57.3 parts by weight of a 48.5 wt % aqueous sodium hydroxide solution, 9.9 parts by weight of water, and 0.15 part by weight of a crosslinking agent (N,N'-methylenebisacrylamide) were added to 125 parts by weight of an 80 wt % aqueous acrylic acid solution to prepare a solution A. The solution A had a monomer concentration of 60% by weight and a degree of neutralization of 50% by mole.

A nitrogen gas was passed into the solution A to remove oxygen, and the solution A was then applied through a dropping nozzle onto a nonwoven fabric of rayon (porosity 90%, weight per unit area 100 g/m$^2$) in such a manner that the solution applied formed a linear pattern. The nonwoven fabric was then irradiated with an electron beam (5 Mrad), and passed through a drying oven to remove water contained in the resultant water-absorptive polymer to give a water-absorptive composite J with the amount of the polymer borne on the nonwoven fabric being 200 g/m$^2$. The results are shown in Table 1.

COMPARATIVE EXAMPLE 4

57.3 parts by weight of a 48.5 wt % aqueous sodium hydroxide solution, 9.9 parts by weight of water, and 0.15 part by weight of a crosslinking agent (N,N'-methylenebisacrylamide) were added to 125 parts by weight of an 80 wt % aqueous acrylic acid solution to prepare a solution A. The solution A had a monomer concentration of 60% by weight and a degree of neutralization of 50% by mole.

A nitrogen gas was passed into the solution A to remove oxygen, and the solution A was then applied on a nonwoven fabric of rayon (porosity 90%, weight per unit area 100 g/m$^2$) through a spray nozzle. The nonwoven fabric was held in an atmosphere of a 0.4% aqueous ammonium persulfate solution atomized by an ultrasonic atomizer for 20 seconds and then held in an atmosphere of a 0.2% aqueous sodium hydrogensulfite solution atomized by the ultrasonic atomizer for 20 seconds, thereby initiating the polymerization reaction. The nonwoven fabric was then held in a nitrogen atmosphere for 60 min. The nonwoven fabric was then passed through a drying oven to remove water contained in the resultant water-absorptive polymer to give a water-absorptive composite K with the amount of the polymer borne on the nonwoven fabric being 200 g/m$^2$. The results are shown in Table 1.

COMPARATIVE EXAMPLE 5

A mixture of 90 parts by weight of sodium polyacrylate having an average molecular weight of 250000 with 24 parts by weight of acrylic acid, 0.7 part by weight of ammonium persulfate, and 0.08 part by weight of a crosslinking agent (N,N'-methylenebisacrylamide) were dissolved in 118 parts by weight of deionized water to prepare a homogeneous, viscous solution A.

The solution A was applied through a nozzle having a bore diameter $\Phi$ of 500 $\mu$m onto a nonwoven fabric of rayon (porosity 90%, weight per unit area 100 g/m$^2$) in such a manner that the solution applied formed a dot pattern. The solution thus applied on the nonwoven fabric was subjected to polymerization in a dryer, tent at 80° C. and purged with nitrogen, to prepare a water-absorptive composite L with the amount of the polymer borne on the nonwoven fabric being 200 g/m$^2$. The results are shown in Table 1.

COMPARATIVE EXAMPLE 6

80.2 parts by weight of a 48.5 wt % aqueous sodium hydroxide solution, 98.3 parts by weight of water, 0.15 part by weight of a crosslinking agent (N,N'-methylenebisacrylamide), and 3.0 parts by weight of sodium persulfate as a polymerization initiator were added to 125 parts by weight of an 80 wt % aqueous acrylic acid solution to prepare a solution A. The solution A had a monomer concentration of 40% by weight and a degree of neutralization of 70% by mole.

A nitrogen gas was passed into the solution A to remove oxygen, and the solution A was then homogeneously sprayed onto a nonwoven fabric of polypropylene/polyethylene (porosity 98%, weight per unit area 100 g/m$^2$) through a dropping nozzle. The nonwoven fabric with the solution A applied thereon was then allowed to stand for 20 minutes in a dryer, kept at 70° C. and purged with nitrogen, to conduct polymerization, and dried at 100° C. in vacuo to prepare a water-absorptive composite M with the amount of the polymer borne on the nonwoven fabric being 200 g/m$^2$. The results are shown in Table 1.

TABLE 1

| Example/Comparative Example | Ex. 1 | Ex. 2 | Ex. 3 | Ex. 4 | Ex. 5 | Ex. 6 | Ex. 7 | Comp. Ex. 1 | Comp. Ex. 2 | Comp. Ex. 3 | Comp. Ex. 4 | Comp. Ex. 5 | Comp. Ex. 6 |
|---|---|---|---|---|---|---|---|---|---|---|---|---|---|
| Water-absorptive composite | A | B | C | D | E | F | G | H | I | J | K | L | M |
| Pattern of polymer particles on substrate | Dot pattern | Dot pattern | Dot pattern | Dot pattern | Dot pattern | Lattice pattern | Dot pattern | No pattern*, partly impregnated into substrate | Dot pattern | Line pattern, partly impregnated into substrate | No pattern*, partly impregnated into substrate | Dot pattern | Dot pattern |
| Average diameter of polymer particles (μm) | 200 | 250 | 230 | 200 | 200 | 400 | 200 | Particles not formed | 180 | Particles not formed | Particles not formed | 5000 | 500 |
| Saline absorption capacity (g/g) | 35 | 34 | 36 | 38 | 34 | 34 | 34 | 13 | 27 | 15 | 18 | 17 | 20 |
| Rate of water absorption (g/g) | 23 | 22 | 24 | 28 | 26 | 18 | 22 | 4 | 17 | 5 | 3 | 5 | 10 |
| Concentration of residual unreacted monomer (ppm) | 200 | 200 | 200 | 200 | 80 | 300 | 250 | 8000 | 150 | 3000 | 3500 | 500 | 2500 |
| Percentage retention A' (%) | 98 | 97 | 98 | 96 | 95 | 92 | 99 | 70 | 30 | 60 | 65 | 80 | 90 |
| Percentage retention A (%) | 85 | 80 | 90 | 92 | 89 | 78 | 91 | 55 | 20 | 45 | 50 | 65 | 50 |

Note) *: Polymer particles are spread over the whole surface of the substrate.

We claim:

1. A process for producing a water-absorptive composite which comprises a fibrous substrate bearing water-absorptive polymer particles, said water-absorptive composite having the following physical characteristics (1) to (4):

(1) a porosity of a substrate of 50 to 99.5%;
    (2) a primary particle diameter of said polymer particles of 50 to 1000 μm;
    (3) an amount of said polymer particles of 10 to 500 g per m$^2$ of said substrate; and
    (4) a percentage retention (A) of said polymer particles, defined by the following equation, of not less than 60%:

$$A(\%) = \frac{W_0 - w}{W_0} \times 100$$

wherein $W_0$ represents the dry weight (g) of a water-absorptive polymer in the following sample, and w represents the dry weight (g) of a water-absorptive polymer fallen from said sample,
    w being measured by a method wherein physiological saline is absorbed into a sheet sample, having a size of 60 mm×300 mm and a thickness of 0.5 to 20 mm, of a water-absorptive composite until the absorption reaches the saturation, the sample is then put on a stone table; in iron roller with a smooth surface, having a diameter of 105 mm, a width of 60 mm and a weight of 4 kg, is reciprocated on said sample five times at a speed of 10 cm/sec, and the weight, after drying, of a water-absorptive polymer fallen from said sample is measured as the w value comprising the steps of:
    allowing first and second liquids to collide against each other in a gas phase, thereby preparing a reaction mixture;
    applying the resultant reaction mixture, which is in the course of polymerization, dropwise onto a fibrous substrate; and
    allowing said polymerization to proceed and finish on said substrate,
    wherein the degree of polymerization when said reaction mixture reaches said substrate is 3–90%
    wherein said first liquid comprises an aqueous polymerizable monomer solution containing either one of an oxidizing agent and a reducing agent which together constitute a redox polymerization initiator; and
    said second liquid comprises an aqueous solution containing the other one of said oxidizing and reducing agents and optionally a polymerizable monomer.

2. The process according to claim 1, wherein the polymerizable monomer is composed mainly of an organic unsaturated carboxylic acid or a salt thereof.

3. The process according to claim 2, wherein the polymerizable monomer is composed mainly of acrylic acid with not less than 20% by mole of the carboxyl group being neutralized with an alkali metal salt or an ammonium salt.

4. The process according to claim 1, wherein the redox polymerization initiator comprises hydrogen peroxide as the oxidizing agent and L-ascorbic acid or an alkali metal salt of L-ascorbic acid as the reducing agent.

* * * * *